United States Patent [19]

Czaja et al.

[11] 4,121,041

[45] Oct. 17, 1978

[54] 7-(AMIDINOTHIO)ACETAMIDO-7-METHOXY CEPHALOSPORINS

[75] Inventors: Robert F. Czaja, Scotch Plains; Edward J. J. Grabowski, Westfield, both of N.J.

[73] Assignee: Merck & Co., Inc., Rahway, N.J.

[21] Appl. No.: 765,477

[22] Filed: Feb. 4, 1977

[51] Int. Cl.² ............... C07D 501/40; A61K 31/545
[52] U.S. Cl. .................................... 544/21; 424/246
[58] Field of Search ................ 260/243 C; 544/21

[56] References Cited

U.S. PATENT DOCUMENTS

| | | | |
|---|---|---|---|
| 3,646,025 | 2/1972 | Crast, Jr. | 260/243 C |
| 3,839,329 | 10/1974 | Breuer et al. | 260/243 C |
| 3,905,963 | 9/1975 | Webber | 260/243 C |
| 3,960,845 | 6/1976 | Hiraoka et al. | 260/239.1 |

*Primary Examiner*—Donald G. Daus
*Assistant Examiner*—Diana G. Rivers
*Attorney, Agent, or Firm*—Hesna J. Pfeiffer; Julian S. Levitt

[57] ABSTRACT

New 7-(Amidinothio)acetamido-7-methoxy-3-carbamoyloxymethyl-3-cephem-4-carboxylic acid compounds are prepared which are useful as antibacterial agents, especially *Pseudomonas*.

3 Claims, No Drawings

7-(AMIDINOTHIO)ACETAMIDO-7-METHOXY CEPHALOSPORINS

SUMMARY OF THE INVENTION:

7-(Amidinothio)acetamido-7-methoxy-3-carbamoyloxymethyl-3-cephem-4-carboxylic acid compounds are provided having the structural formula

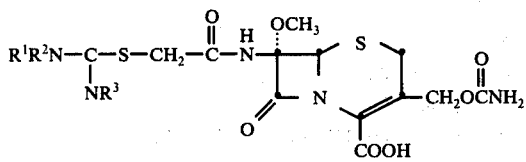

wherein $R^1$, $R^2$, and $R^3$ can be the same or different and can be hydrogen, loweralkyl of 1-5 carbon atoms, or phenyl. $R^1$ and $R^2$ can also be linked to form a cycloalkyl group around the nitrogen atom having 3-6 carbon atoms. Preferably, $R^1$, $R^2$, and $R^3$ are all hydrogen. The compounds can be prepared as any of a number of labile esters, including benzyl, benzhydryl, methoxymethyl, t-butoxycarbonyl, etc., or as acid addition salts such as the hydrochloride or hydrobromide.

These compounds are prepared by reaction of the appropriate thiourea

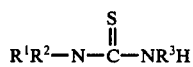

with a 7-chloro or 7-bromoacetamido cephem compound

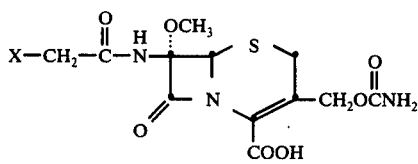

wherein X is Cl or Br. The compound of Formula 3 can be employed in the reaction as either the free acid or as any of the commonly employed ester forms.

The products, Formula 1, have antibiotic activity, especially against various Pseudomonas strains.

DETAILED DESCRIPTION OF THE INVENTION

The starting materials for this invention, those of Formula 3 above, can be prepared from the natural product, 3-carbamoyloxymethyl-7-(aminoadipoylamino)-7-methoxy-3-cephem-4-carboxylic acid, isolated from either S. lactamdurans or S. clavulingerus, NRRL 3802, and NRRL 3585, respectively. The most convenient method uses the bis-di-methoxymethyl ester of the N-tosyl blocked natural product in reaction with chloroacetylchloride in the presence of molecular sieves, a reaction process disclosed in more detail in Weinstock, U.S. Ser. No. 420,418, filed Nov. 30, 1973, now abandoned; U.S. Ser. No. 507,473, filed Sept. 23, 1974, now abandoned; and U.S. Ser. No. 689,408, filed May 24, 1976. Following deblocking of the ester group, the 7-chloroacetamido compound is reacted with the appropriate thiourea.

The thiourea compounds, Formula 2 above, are all commercially available. The preferred compound is thiourea, so that all $R^1$, $R^2$, and $R^3$ are hydrogen.

The two reactants, of Formulas 2, and 3, are mixed together in approximately equal molar amounts, although the thiourea compound can conveniently be employed in approximate 2-5 times molar excess. The reactants are mixed in a solvent preferably a lower alkanol, such as methanol, although the identity of the solvent is not critical to the success of the reaction, and any common solvent in which both reactants are soluble to a great extent will be useful. The reaction proceeds easily at ambient temperatures, within 12-60 hours. Stirring can be optionally employed during the reaction process. Following reaction completion, insolubles are removed by filtration, and the desired product isolated using standard techniques. Generally the product is isolated as the hydrochloride, and the other salt or ester derivatives can be easily prepared using techniques known to these in the art. It will be seen that if the bromoacetamido derivative of Formula 3 above is the starting material, the salt form is that of the hydrobromide.

The compounds of this invention can be used as antibiotic agents to cure or control infections in humans and animals, having antibacterial activity against S. aureus, V. percolans, S. marcescens, Corynebacterium species, M. flavces, Pseudomonas species. For instance, the compound 7-(amidinothio)acetamido-7-methoxy-3-carbamoyloxymethyl-3-cephem-4-carboxylic acid has an inhibition zone diameter of 21 mm. and 16 mm, respectively, against P. stutzeri and P. aeruginosa, at a concentration of 62.5µg/ml. The other compounds within the structure defined by Formula 1 have similar potency. The compounds of Formula 1 can be formulated into any of a number of known compositions for cephalosporin antibiotics, including injection in a sterile water solution, as the hydrochloride, packaged in unit dosage form of between 250 mg. – 1000 mg. The effective dosage levels of the compound are generally between 80 – 120 mg/kg body weight, for human use as injections.

This invention is further illustrated by the following examples.

EXAMPLE 1

Preparation of 3-Carbamoyloxymethyl-7-methoxy-7-(amidinothio)acetamido-3-cephem-4-carboxylic acid Step A: Preparation of 7-Chloroacetamido Ester Derivatives A mixture of 7.68 g. (10 mmoles) of 90% methoxymethyl(3-carbamoyloxymethyl-7-methoxy-7-(N-tosylamino)-adipoylamino, methoxymethyl ester 3-cephem-4-carboxylate, 4.52 g. (40 mmoles) of chloroacetylchloride and 7.5 g. of type 4A molecular sieves (powder, 600 mesh) and 70 ml. of 1,2-dichloroethane was stirred vigorously for 20 hours at 65°. The reaction was then filtered and the filtrate was concentrated to a volume of 30 ml. Approximately 150 ml. of hexane was added and crude product oiled out. The oil was redissolved in 20 ml. of 1,2-dichloroethane and the resulting solution treated with 150 ml. of hexane. Product oiled out. It was degassed in vacuo at room temperature to give 7.6 g. of methoxymethyl-3-carbamoyloxymethyl-7-methoxy-7-chloroacetamido-3-cephem-4-carboxylate.

Step B: Preparation of 3-Carbamoyloxymethyl-7-methoxy-7-chloroacetamido-3-cephem-4-carboxylic Acid The above material prepared in Step A, (7.6 g.) was dissolved in 70 ml. of 1,2-dichloroethane and cooled to 5°. One hundred twenty ml. of methanol was added followed by 20 ml. of concentrated hydrochloric acid. The mixture was warmed to 15° and stirred at 15° for 2½ hours and cooled to 5°. To this mixture was added a cooled solution (5°) of 30 g. of sodium bicarbonate in 300 ml. of water. The cold aqueous layer was then acidified with 40 ml. of concentrated hydrochloric acid and product extracted into 100 ml. of ethyl acetate. The aqueous layer was then washed with 3 × 50 ml. of ethyl acetate. The organic layers were combined, washed with 75 ml. of saturated aqueous sodium chloride, dried over anhydrous sodium sulfate and concentrated in vacuo to give 4.92 g. of 7-chloroacetamido acid derivative of Step B.

Step C: Preparation of 3-Carbamoyloxymethyl-7-methoxy-7-(amidinothio)acetamido-3-cephem-4-carboxylic Acid A mixture of 0.400 g. (1 mmole) of 7-chloroacetamido acid derivative of Step B and 0.160 g. (2 mmoles) of thiourea in 20 ml. of methanol was stirred for 48 hours at room temperature. The insolubles were removed by filtration. The filtrate was concentrated in vacuo. The concentrate on trituration with 2 × 50 ml. of 9:1 ether:-methanol gave 0.210 g. of 3-carbamoyloxymethyl-7-methoxy-7-(amidinothio)acetamido-3-cephem-4-carboxylic acid, H nmr (DMSO-$d_6$, TMS) $\delta$ 3.4 (5H, S—$CH_2$—C≡C and $OCH_3$), $\delta$ 4.2 (2H, s, S—$CH_2$—C=O), $\delta$ 4.7 (2H, s, $CH_2$—O); $\delta$ 5.1 (1H, s,

$\delta$ 6.6 (2H, s, $OCONH_2$).

What is claimed is:
1. The compound having the following formula

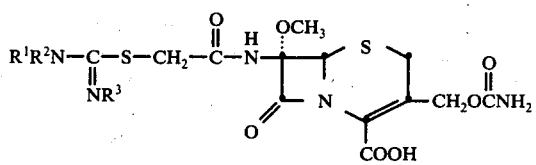

wherein $R^1$, $R^2$ and $R^3$ are the same or different and are hydrogen, loweralkyl of 1–5 carbon atoms, or phenyl.

2. The compound of claim 1 in which $R^1$, $R^2$, and $R^3$ are the same.

3. The compound of claim 2 in which $R^1$, $R^2$, and $R^3$ are hydrogen.